United States Patent [19]

Bock et al.

[11] Patent Number: 5,496,256

[45] Date of Patent: Mar. 5, 1996

[54] ULTRASONIC BONE HEALING DEVICE FOR DENTAL APPLICATION

[75] Inventors: Robert T. Bock, Brewster, N.Y.; John P. DeLuca, Washington, D.C.

[73] Assignee: Sonex International Corporation, Brewster, N.Y.

[21] Appl. No.: 257,773

[22] Filed: Jun. 9, 1994

[51] Int. Cl.⁶ .......................... A61B 17/56; A61C 8/00; A61C 19/06; A61F 5/00
[52] U.S. Cl. ................. 601/2; 607/51; 433/174; 433/215
[58] Field of Search ................. 601/2; 607/50, 607/51; 433/86, 174, 215; 623/16; 128/653.1, 660.01

[56] References Cited

U.S. PATENT DOCUMENTS

| | | | |
|---|---|---|---|
| 3,380,446 | 4/1968 | Martin | 601/2 |
| 4,127,125 | 11/1978 | Takemoto et al. | 601/2 |
| 4,148,309 | 4/1979 | Reibel | 601/2 |
| 4,153,060 | 5/1979 | Korostoff et al. | 607/51 |
| 4,175,565 | 11/1979 | Chiarenza et al. | 607/51 |
| 4,244,373 | 1/1981 | Nachman | 607/50 |
| 4,530,360 | 7/1985 | Duarte | 607/51 |
| 4,781,591 | 11/1988 | Allen | 607/51 |
| 4,905,671 | 3/1990 | Senge et al. | 601/4 |
| 5,103,806 | 4/1992 | McLeod et al. | 601/2 |
| 5,161,521 | 11/1992 | Kasahara et al. | 601/2 |
| 5,284,143 | 2/1994 | Rattner | 128/653.1 |
| 5,330,357 | 7/1994 | Keller | 433/215 |

FOREIGN PATENT DOCUMENTS

| | | | |
|---|---|---|---|
| 8809190 | 12/1988 | European Pat. Off. | 601/2 |
| 1146032 | 3/1985 | U.S.S.R. | 433/215 |

Primary Examiner—Krista M. Zele
Attorney, Agent, or Firm—Watson, Cole, Grindle & Watson

[57] ABSTRACT

Non-invasive apparatus for accelerating the process of jawbone healing and regeneration, reattachment of traumatically loosened teeth to the jawbone, or osseointegration of implants in a patient, including at least one piezoelectric transducer and connections to transmit ultrasonic frequency electrical current to the piezoelectric transducer. The ultrasonic frequency electrical current transmitted to the piezoelectric transducer causes the transducer to contract and expand volumetrically in response to a changing electrical field to generate pressure wave vibrations of ultrasonic frequency that are coupled to the bone.

13 Claims, 9 Drawing Sheets

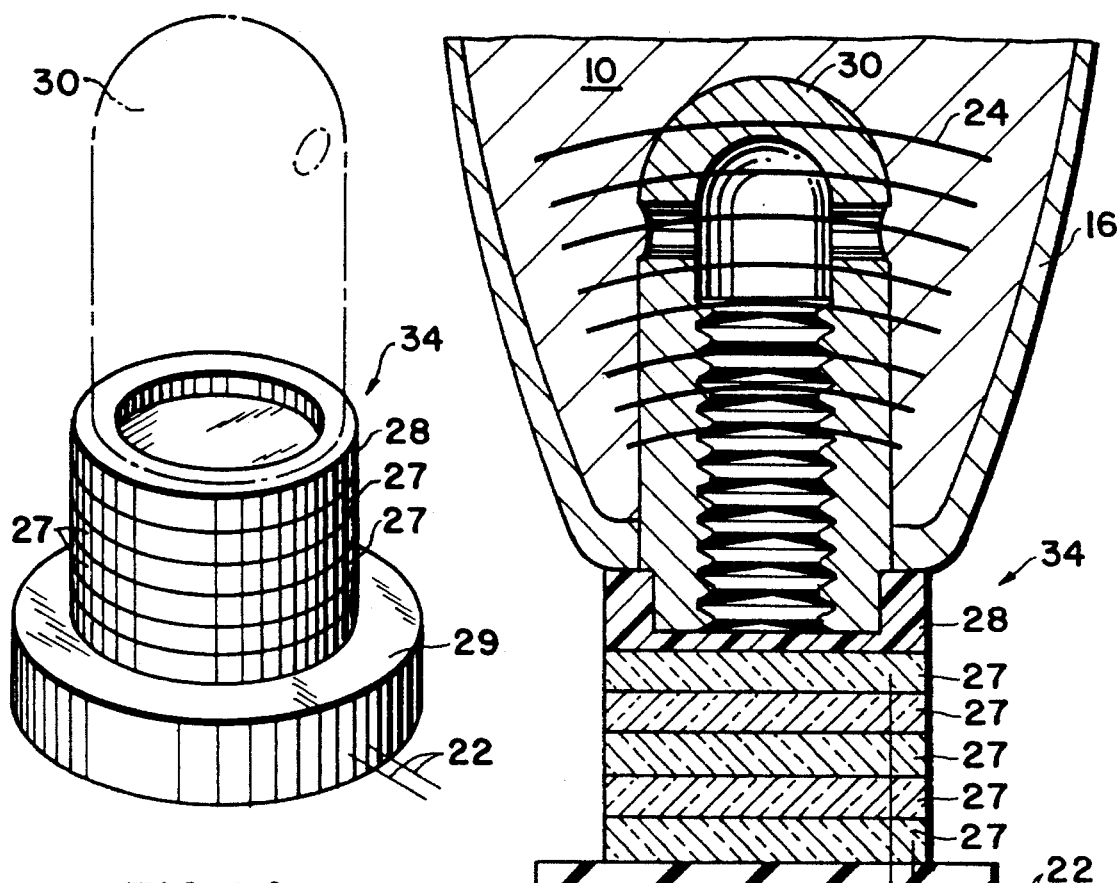
FIG.6A
FIG.6B
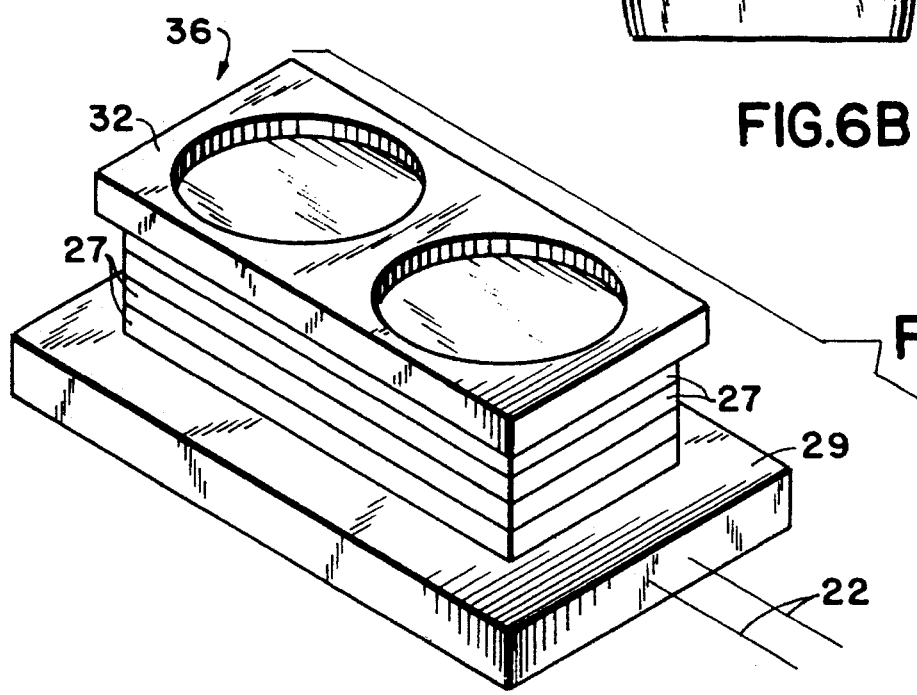
FIG.7A

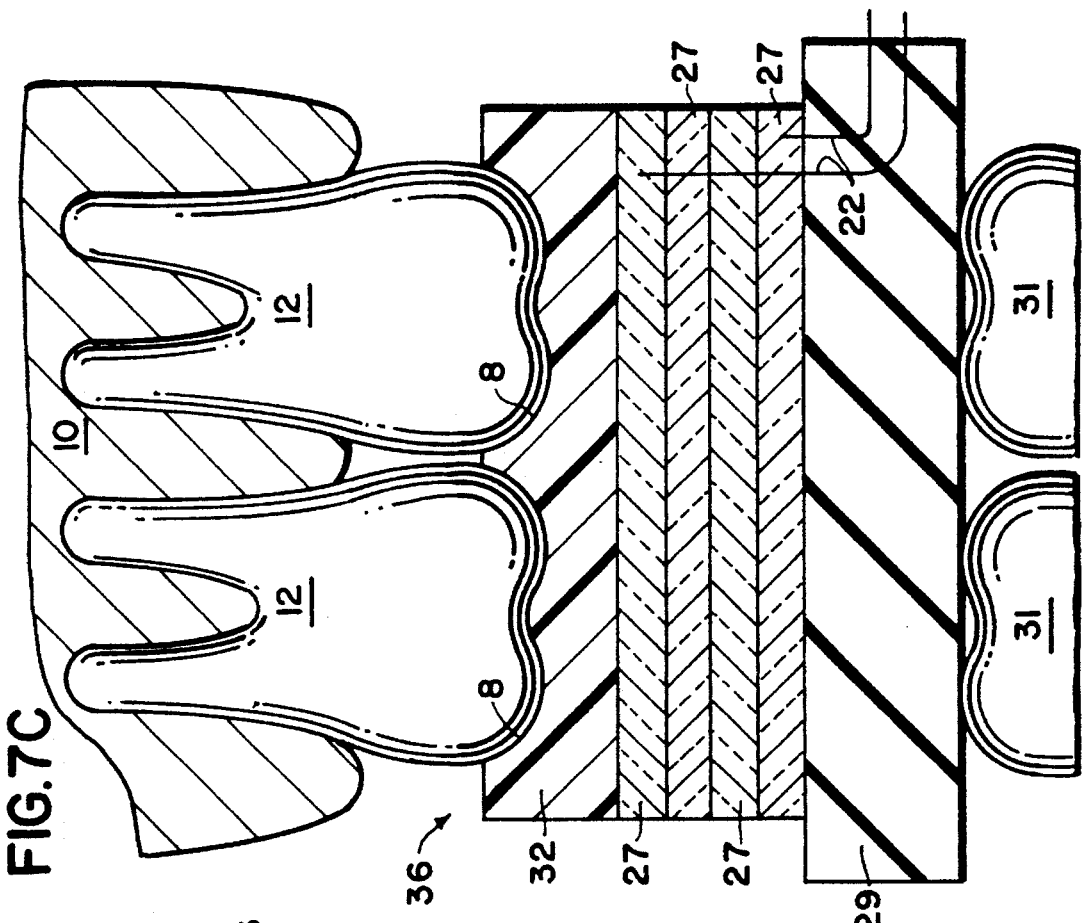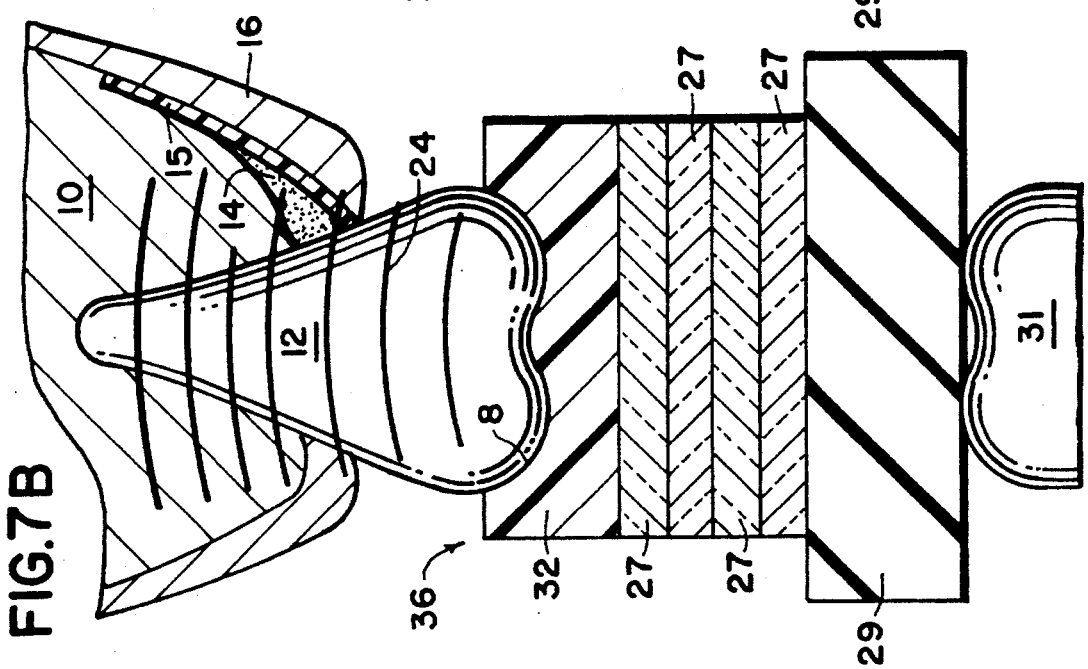

ULTRASONIC BONE HEALING DEVICE FOR DENTAL APPLICATION

BACKGROUND OF THE INVENTION

This invention relates to bone healing devices. More particularly, the invention is concerned with an apparatus for facilitating the use of ultrasonic energy to significantly accelerate repair, grafting and healing of bone of patients impacted by periodontitis and other dental diseases effecting the oral cavity. The invention is particularly effective to improve the success and speed of osseointegration of dental implants and reattachment of traumatically loosened teeth.

A later stage of the periodontal disease in adults is the deterioration and loss of bone supporting the teeth. Numerous attempts have been made to reverse the deterioration and to heal the bone in the oral cavity by electrical means. The application of high frequency electrical currents by electrodes piercing the soft tissue and connecting to the bone has been demonstrated to accelerate healing, but it has also increased the possibility of infection in the invaded tissue. Due to the complications of infections, these procedures are no longer in use, and in general, the medical community relies on the natural, however long, healing process.

During currently employed directed tissue regeneration procedures, the surgeon typically separates the gums from the deteriorated section of the jawbone, forming a pocket adjacent the surface of the bone that is filled with a two component system comprising freeze dried crushed bone and medication. The medication is sealed by a membrane implant and the membrane is sealed in place by reattachment of the gums around the membrane.

The final stage of periodontal disease is exemplified by extensive deterioration of bone resulting in the loss of teeth. Teeth can be replaced by implants, which involves a surgical procedure consisting of the installation of metal posts into the jawbone; the osseointegration of the posts and the bone; and the installation of artificial teeth onto the implanted posts utilizing anchoring screws. The implanted posts typically are coated with either plasma-sprayed titanium, hydroxyapatite, or other similar materials. Finely ground filler materials are used to reinforce porous bone and implant interface and to improve osseointegration of implants. The materials include freeze dried bone, natural coral and synthetic materials. While the addition of these materials generally improve the strength of porous and inadequate bone, the speed of healing and a complete osseointegration is still controlled by the natural healing process, which at times takes as long as six months. The probability of movement of the implants during the healing time, resulting in a less than adequate bond, is proportional with the elapsed time required for osseointegration.

A further problem associated with the repair, grafting and healing of bone is that bacterial contamination, which despite all efforts, eventually occurs at the site, can impede the process of healing. Accordingly, it is desired to reduce or impede bacterial contamination to thereby improve and accelerate healing.

What has occurred to date is that notwithstanding the teachings of the prior art, the ability to speed up healing effectively, inexpensively, and easily in a home environment has remained unsolved.

SUMMARY OF THE INVENTION

Responding to the above-described unresolved needs, the invention provides a non-invasive method, by periodic (e.g., daily) application of ultrasound in the oral cavity, to speed up healing of bone and osseointegration of implants and to speed up the reattachment of teeth to the jawbone after traumatic loosening of teeth. The invention employs a piezoelectric device.

In one embodiment, the invention utilizes at least one piezoelectric transducer positioned in the oral cavity, driven by ultrasonic frequency current from a power supply located outside of the oral cavity, and radiating high frequency low intensity ultrasonic energy from the transducer through the gingival tissues or the teeth or both into the jawbone.

According to a feature of the invention, a relatively inexpensive disposable ultrasonic transducer may be fitted to the anatomy of a patient. The transducer may be used with a reusable ultrasonic power supply that could be utilized by multiple patients in a hospital setting. The external power supply may also be reused by transferring to another patient after that the full course of treatment has been completed by one in a home environment.

Another feature of the invention is a method for controlled and accurate positionment of the transducer at the optimum location for the treatment. The accuracy of such positionment is independent of the skill and the dexterity of the patient.

Yet another feature of the invention is to facilitate the absorption of the medication into the soft and hard tissues of the oral cavity. Further aspects, features and advantages of the invention will be apparent from the examination of the specification, drawings and claims.

Another feature of the invention is to reduce bacterial contamination by retarding bacterial growth and propagation at the site.

BRIEF DESCRIPTION OF THE DRAWINGS

In the accompanying drawings, certain exemplary modes of carrying out the present invention are shown for illustrative purposes:

FIG. 6A is a perspective view of an embodiment of the invention for facilitating osseointegration where the transducer is constructed as a multilayer stacked piezoelectric device that is held in position during the treatment by the teeth of the opposing jaw;

FIG. 6B is a cross-sectional view taken along line 6B—6B of FIG. 6A as used during osseointegration of implants;

FIGS. 7A, 7B and 7C show an arrangement similar to FIGS. 6A and 6B employing an elongated transducer device where the ultrasonic energy is transmitted through one or more teeth to the jawbone and the bone healing device is held in place by the teeth of the opposing jaw for use in a directed tissue regeneration procedure;

DESCRIPTION OF THE INVENTION

Figure 1A:
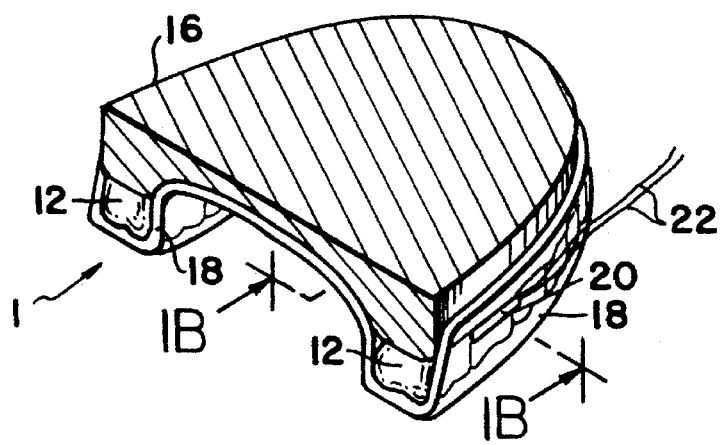
FIG. 1A is a perspective view of an ultrasonic bone healing device according to the invention shown in position adjacent the teeth of a patient.

Referring in detail to the drawings, the reference numerals herein refer to the like numbered elements in the drawings. In the following discussion, unless otherwise qualified, the term "ultrasound" refers to either continuous wave ultrasound or a repetitive burst type ultrasonic modality.

According to one theory, when ultrasonic frequency pressure waves are applied to the bone, the bone creates microcurrents within its structure which enhances the healing process. By bombarding the jawbone with ultrasonic pressure waves through the soft tissue or the teeth, electric current is generated internally within the bone without breaking the skin, providing a non-invasive modality.

According to another theory, osteoblast cell membrane capacitance and the kinetics of the ion binding pathway may be modified by ionic displacement due to the local interfacial pressure waves delivered by the ultrasonic bombardment of the tissue. This ionic displacement may be the physical trigger for a biochemical cascade as predicted by the electrochemical information transfer hypothesis. Other mechanisms may also be causative or contributing factors. However, the invention should not be limited to any particular theory.

Figure 1B:
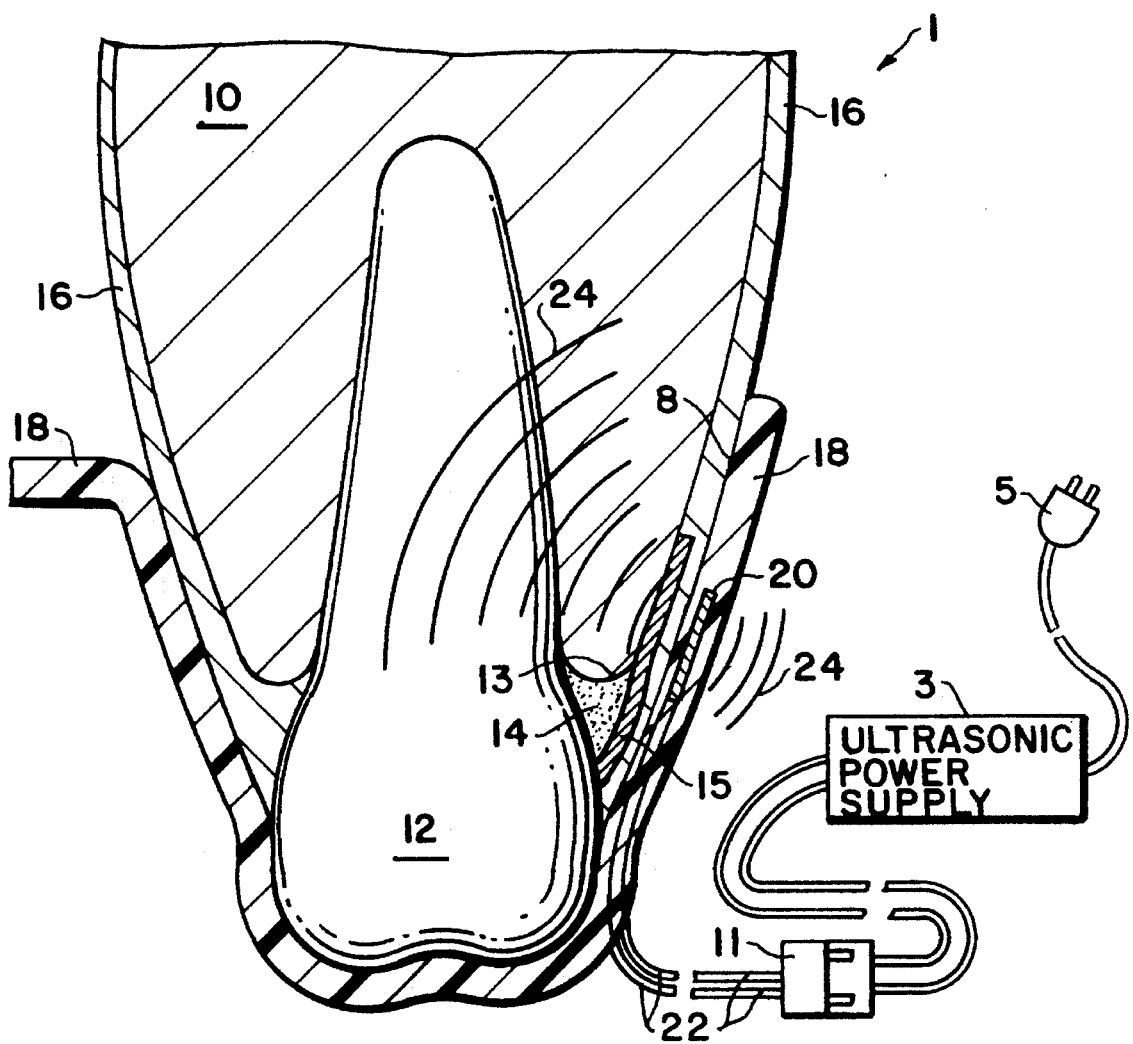
FIG. 1B is a cross-sectional view of the invention taken along line 1B—1B of FIG. 1A as used during the directed tissue regeneration procedure.

An ultrasonic bone healing device 1, in accordance with one form of the present invention, is shown in FIGS. 1A and 1B. The healing device 1 is adapted to be employed within the mouth of a human for accelerating the healing and bone regeneration process. As shown in FIG. 1B, the tooth 12 is secured in the body by bone tissue 10, surrounded by soft gum tissue 16. In the illustrative embodiment, a pocket 13 resulting from gum disease is formed between the bone 10 and soft tissue 16, by recession of bone tissue adjacent the tooth 10. Treatment of the disorder involves implanting a filler material 14, e.g., bone fragments, etc., into the pocket 13 and placing a membrane 15 or cover over the material and under the soft tissue 16.

In the embodiment illustrated, the bone healing device 1 comprises piezoelectric transducer 20 secured in a cast 18 and having connecting wires 22 and a connector 11 that connects the healing device 10 to an external ultrasonic power supply 3. The external ultrasonic power supply 3 draws its power either from a standard household current through connector 5 as shown, or is operated from a battery within the power supply.

When energized, the power supply 3 activates the piezoelectric transducer 20 to produce ultrasonic waves 24, the cast 18 is made of a flexible material that has an interior portion that conforms to the surface of the soft tissue 16 and the teeth 12 surrounding the bone 10 in the affected area. To enhance transmission of the ultrasonic waves 24 through the soft gingival tissue 16 to the bone 10, a thin coating of gel 8 may be applied onto the interior surface of the cast 18.

The intensity of the ultrasonic waves 24 should not cause tissue heating. It has been found that the intensity may be up to approximately 30 mW/cm$^2$ which is below the tissue heating range. The frequency of the waves can be in a range from about 20,000 Hertz to above 5,000,000 Hertz. Preferably, the frequency is about 1.5 MHz.

The ultrasonic waves 24 are conducted through the various structures including the cast 18, the gingival tissue 16, the membrane 15, the medication and bone fragments 14 in pocket 13, into the bone 10 and into the teeth 12. The ultrasonic energy generates microcurrents in the bone 10 and the teeth 12 to enhance the healing and regeneration of the bone 10.

The application of ultrasonic energy as set forth in the above embodiment and in the various embodiments hereafter discussed, also has an additional advantage, namely the reduction of bacterial contamination and inflammation at the healing site. The ultrasonic energy retards and reduces bacterial growth and the inflammation associated with contamination and healing. Thus, the invention promotes and accelerates healing of the bone and the soft tissue by facilitating a decontamination of the site as well as by promoting the generation of microcurrents.

Figure 2A:
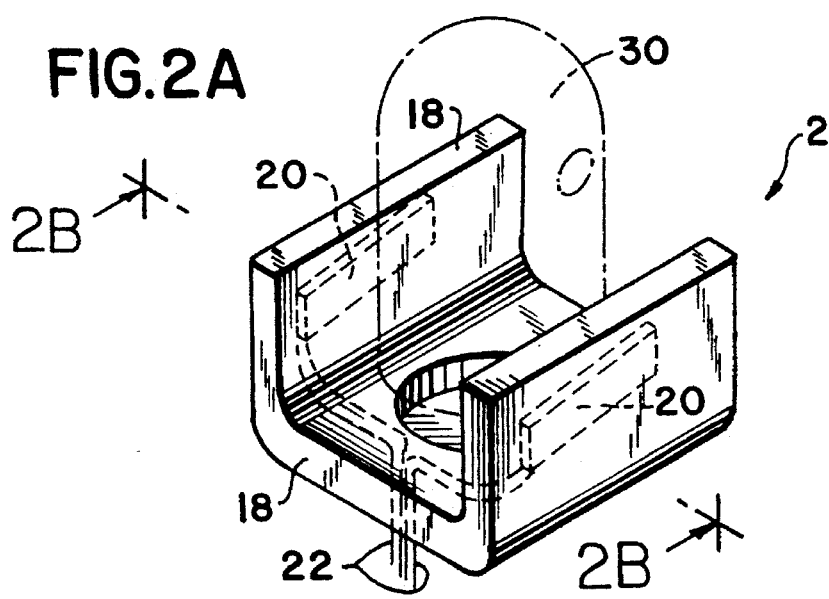
FIG. 2A is a perspective view of another embodiment of the invention for use in osseointegration of implants.
Figure 2B:
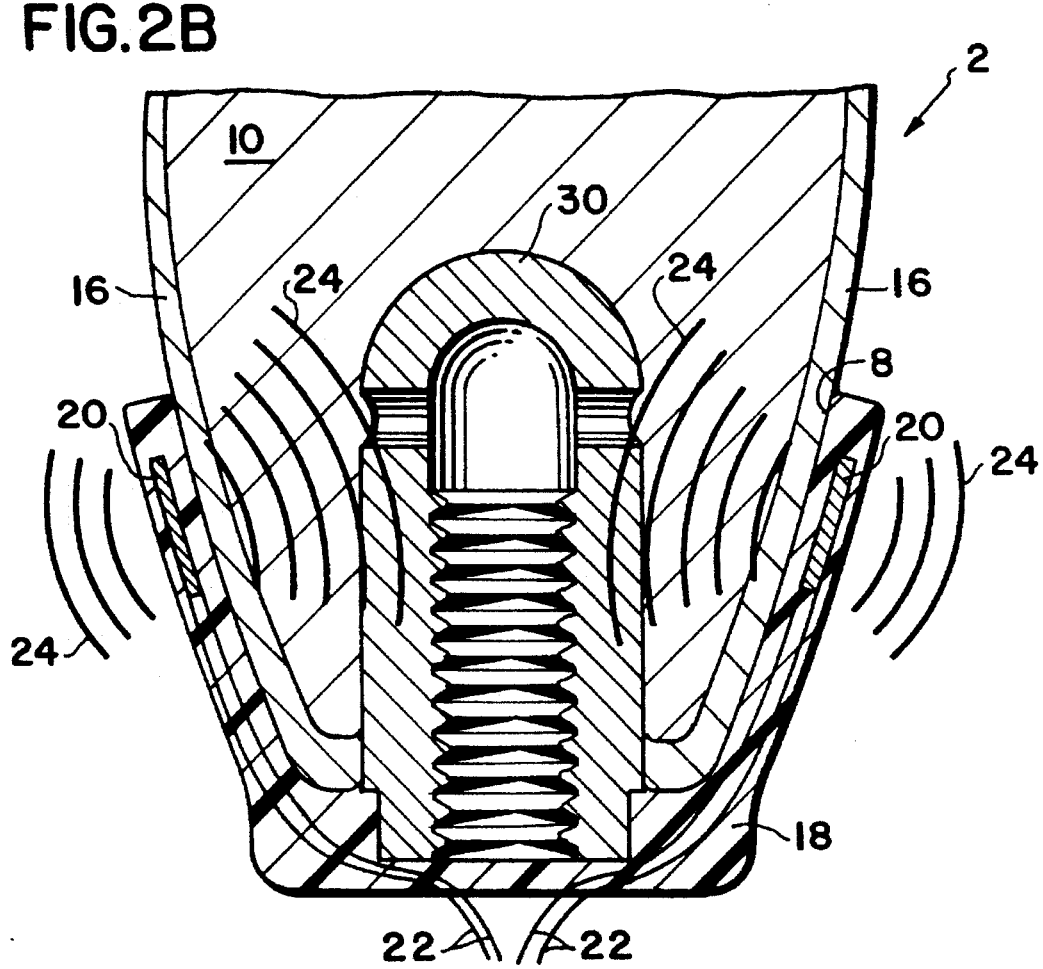
FIG. 2B is a cross-sectional view of the invention taken along line 2B—2B of FIG. 2A as used during osseointegration of implants.

FIGS. 2A and 2B illustrate an embodiment of the invention employing an ultrasonic bone healing device 2 for enhancing the osseointegration process of an implant 30 located in the jawbone 10. The bone healing device 2 comprises a pair of piezoelectric transducers 20, connecting wiring 22 and (as shown in FIG. 1B) common connector 11 that connects to the external ultrasonic power supply 3. The external power supply draws its power either from a standard household current through a connector 5 or is operated from a battery within the power supply.

The piezoelectric transducers 20 are encapsulated in cast 18 made of a flexible material that conforms to the surface of the soft tissue 16 surrounding the jawbone 10. The cast also has a recess for receiving the free end of implant 30. To enhance transmission of the ultrasonic waves 24 through the soft gingival tissue 16, a thin coating of gel 8 is applied onto the cast 18.

The intensity of the ultrasonic waves 24 is regulated so as not to exceed the tissue heating range, e.g., approximately 30 mW/cm$^2$. The frequency of the waves is in the range noted above and is preferably 1.5 MHz.

The ultrasonic waves 24 are conducted through the cast 18 and the gingival tissue 16 into the bone 10 and the implant 30. The ultrasonic energy generates microcurrents in the bone 10 to enhance the healing of the bone 10 and osseointegration of the implant 30.

Figure 3A:
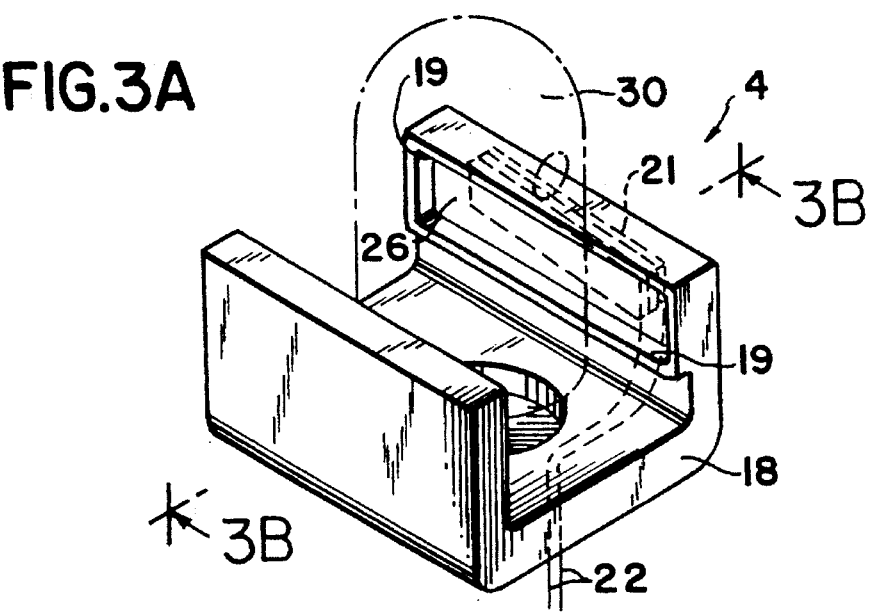
FIG. 3A is a perspective view of an embodiment of the invention employing an ultrasound transmitting gel interface to the skin sealed from the outside environment.
Figure 3B:
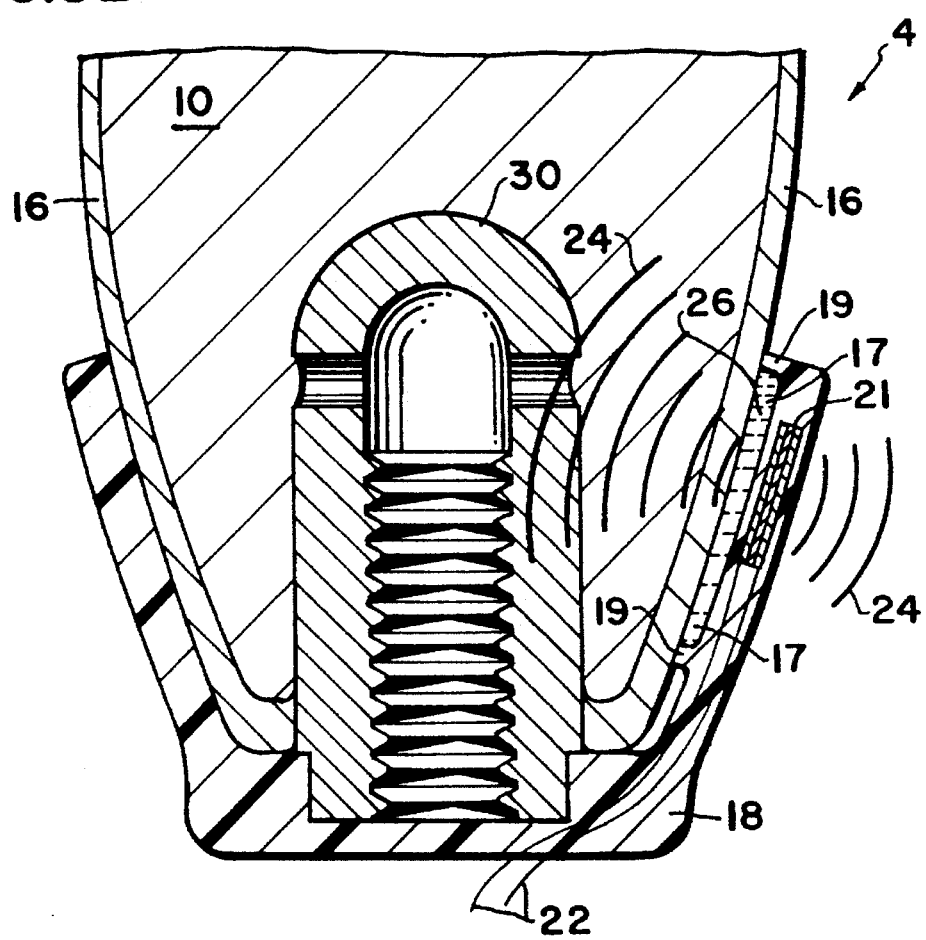
FIG. 3B is a cross-sectional view of the invention taken along line 3B—3B of FIG. 3A as used during osseointegration of implants.

FIGS. 3A and 3B show an embodiment of a bone healing device 4 similar to the arrangement illustrated in FIGS. 2A and 2B in which cast 18 has a pocket 17 formed in the interior surface 26 thereof. The pocket 17 is sealed against the soft tissue 14 by lips 19 which define boundaries of the pocket 17. A volume of gel 26 may be located in the pocket 17 to improve the transmission of the ultrasonic waves 24 emitted from transducer 21 through the soft tissue 16 and into the jawbone 10.

In the arrangement illustrated in FIGS. 3A and 3B, the transducer 21 comprises a multilayer device having two outer layers and an intermediate layer. In operation, the multilayer transducer 21 produces more powerful ultrasonic waves 24.

Figure 4A:
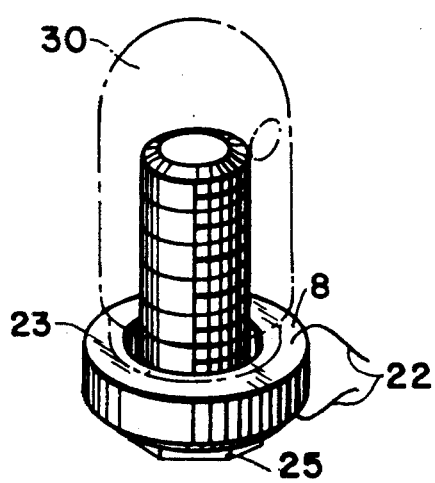
FIG. 4A is a perspective view of an embodiment of the invention for facilitating osseointegration where the transducer is directly attached to the implant.
Figure 4B:
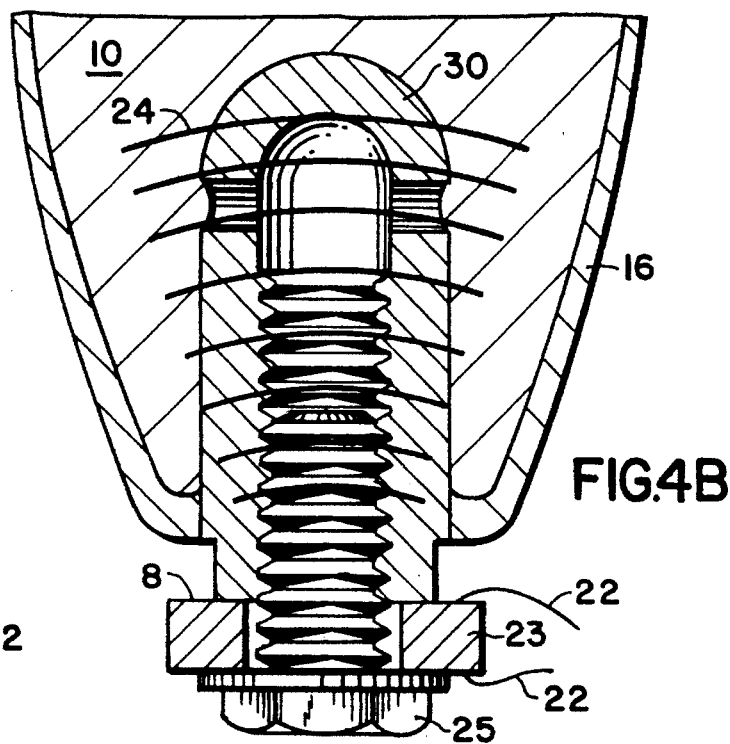
FIG. 4B is a cross-sectional view of the invention taken along line 4B—4B of FIG. 4A as used during osseointegration of implants.

FIGS. 4A and 4B show an embodiment of the invention employing an apertured piezoelectric transducer 23. The transducer 23 is directly attached to the free end of the implant 30 by means of a threaded stud 25 to transmit ultrasonic waves 24 or vibrations directly through the implant 30 and into the jawbone 10. The advantage of this embodiment is that the implant 30 is a good conductor of the ultrasonic waves 24. Thus, the implant 30 conducts the waves 24 directly to the interface between the bone 10 and implant 30 where the osseointegration takes place.

Figure 5A:
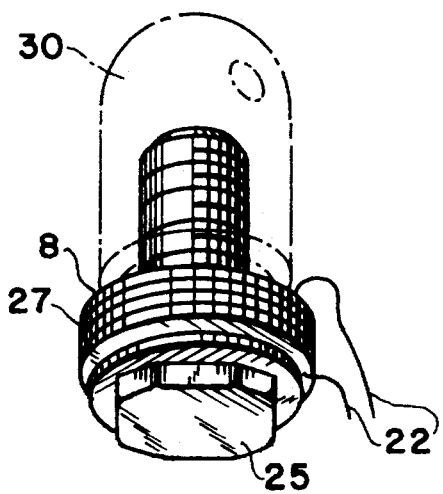
FIGS. 5A and 5B show an embodiment similar to FIGS. 4A and 4B which employs a multilayer stacked piezoelectric transducer device.
Figure 5B:
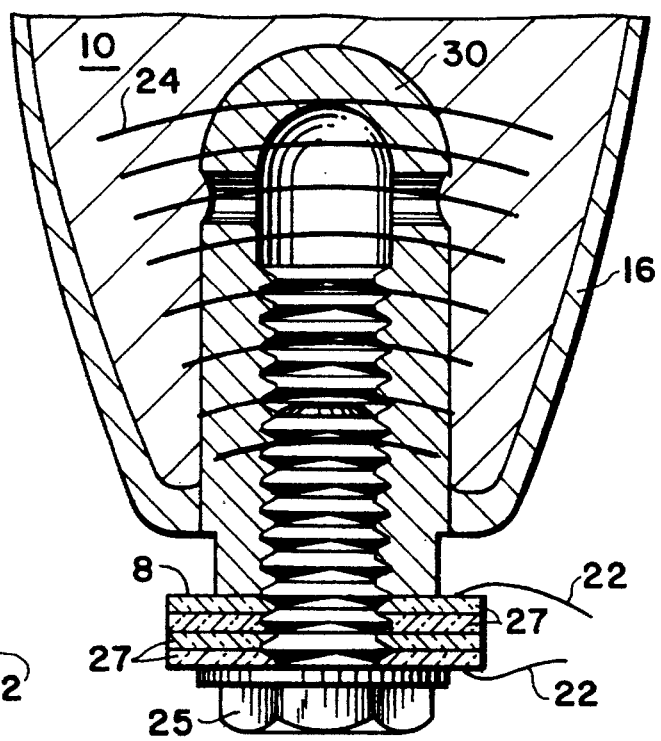

FIGS. 5A and 5B show an arrangement similar to FIGS. 4A and 4B employing a multilayer piezoelectric transducer 27 configuration with increased ultrasonic power output capability.

FIGS. 6A and 6B show another embodiment of the invention employing a bone healing device 34 adapted to engage the free end of the implant 30. In the arrangement illustrated, the device 34 comprises a resilient transducer support 28, an end cap 29 and a transducer 27 therebetween, e.g., in the arrangement illustrated, the transducer 27 is optionally a multilayer device. The end-cap 28 has a recess providing a close fit to free end of the implant 30. The flexible pad 29 cushions the opposing tooth 31 while it holds the bone healing device 34 against the implant 30. The pad 29 also acts to attenuate ultrasonic energy from the side of the transducer 27 opposite to the teeth under treatment. This embodiment makes the daily attachment of the bone healing device 34 to the implant 30 a much easier task so it can be accomplished with ease by the elderly and people with reduced dexterity.

FIGS. 7A–7C show yet another embodiment of the invention in which the bone healing device 36 is an elongated structure similar to the arrangement of FIGS. 6A and 6B. The device 36 is adapted to engage one or more teeth 12 and includes an optional multilayer transducer 27, an intermediate flexible pad 29, a one-piece solid mold end-cap 32 molded to fit the crown of the teeth 12. The pad 29 cushions the opposing teeth 31 while it holds the end cap 32 of the bone healing device 36 against the teeth 12. The ultrasonic waves 24 are transmitted from the piezoelectric crystal stack 27 through the end-cap 32 directly to the teeth 12 and to the jawbone 10 without going through the soft tissue 14. To enhance transmission of the ultrasonic waves 24 into the teeth 12, a thin coating of gel 8 may be applied onto the end-cap 32. The advantage of this embodiment is that the teeth 12 conduct the ultrasonic waves 24 more efficiently than the soft tissue 16. Also, the waves 24 are conducted directly to the jawbone 10 where the healing and bone regeneration must take place. This embodiment also makes the daily attachment of the bone healing device 36 to the teeth 12 a much easier task so it can be accomplished with ease by the elderly and people with reduced dexterity.

Figure 8A:
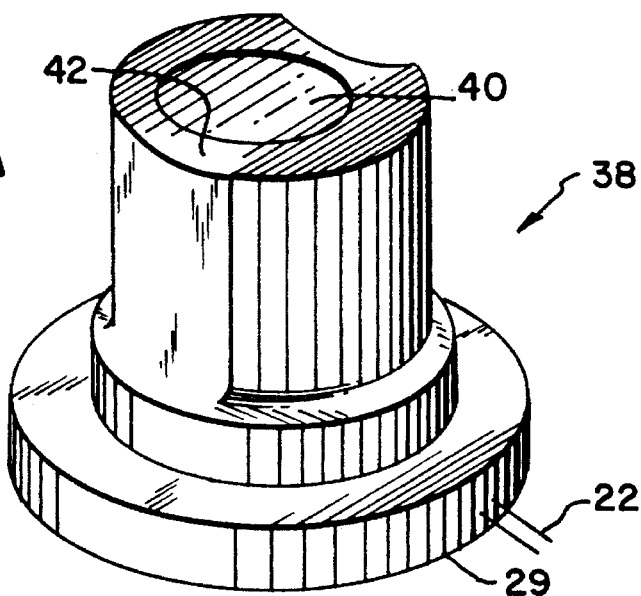
FIGS. 8A, 8B and 8C show an embodiment of the invention similar FIGS. 6A and 6B employing a multilayer transducer.
Figure 8C:
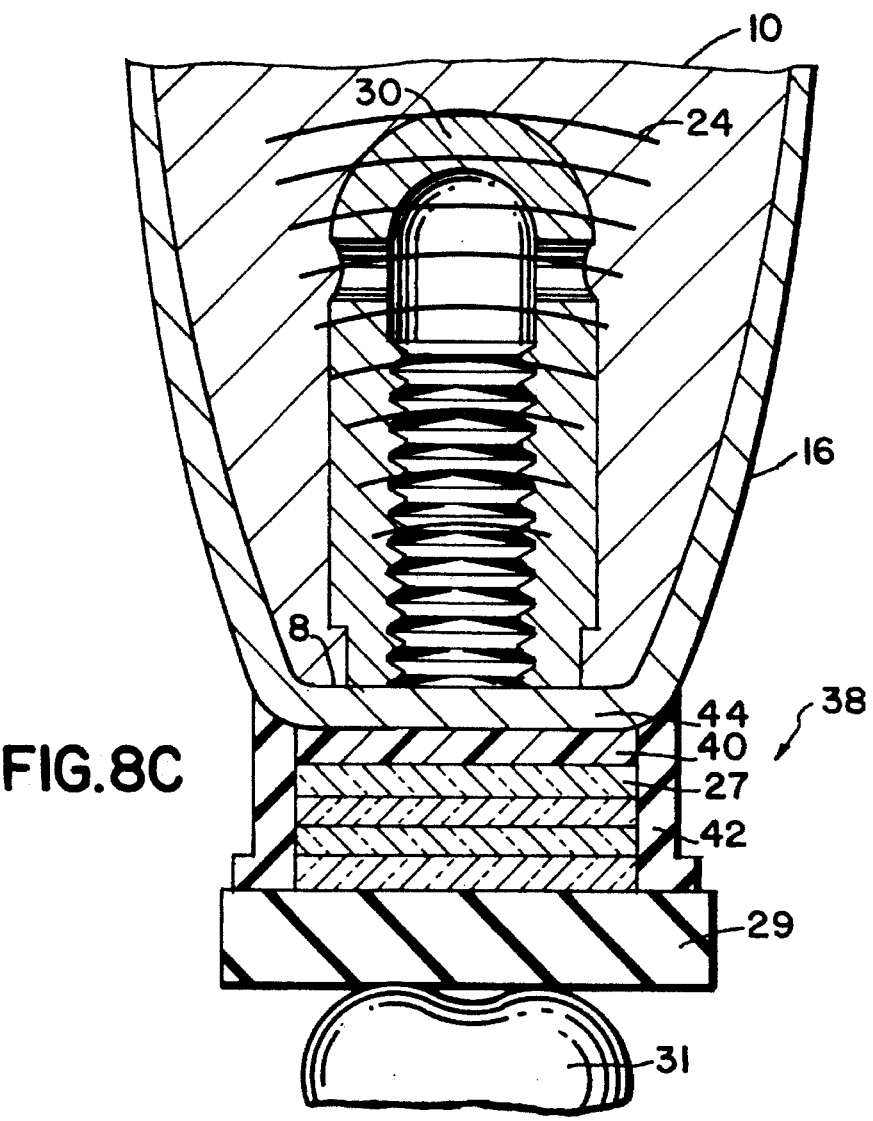
Figure 8B:
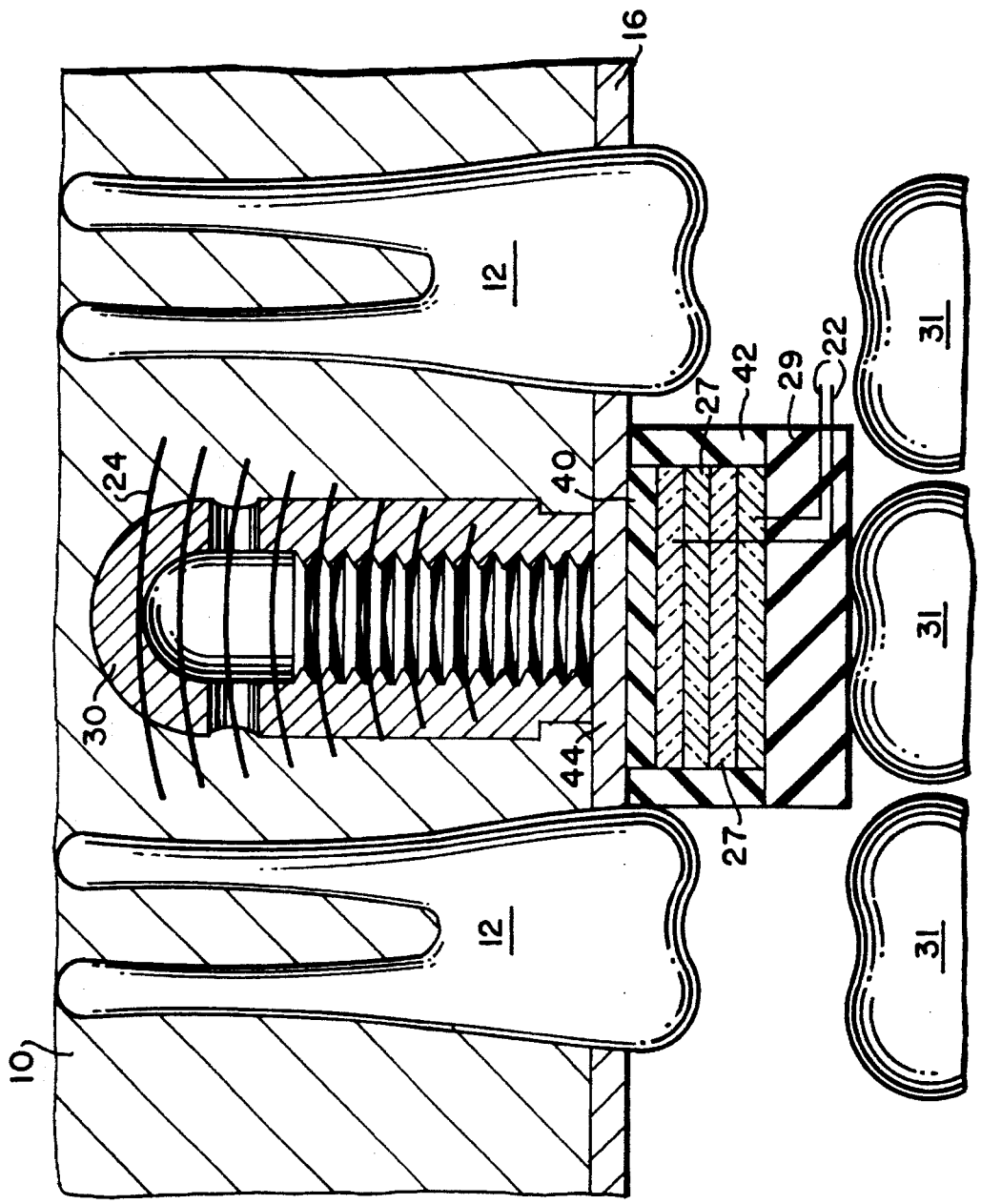

FIGS. 8A–8C show a bone healing device 38 for osseointegration application at the stage of the implantation procedure when the implant is installed into the jawbone but it is still covered with a soft tissue gum flap 44 during the early stages of the osseointegration procedure. In this arrangement, the ultrasonic waves 24 are transmitted via an end-cap 40 of the transducer 27 through the soft tissue gum flap 44 directly into the implant 30. The advantage of this embodiment is that the implant 30 conducts the ultrasonic waves 24 evenly to the jawbone interface where the osseointegration takes place. The end-cap 40 is cast to spatially conform the soft tissue end flap 44 of the gum covering the implant. The transmission of the waves 24 is enhanced by the application of a thin layer of gel 8. The device 38, like other embodiments, may utilize a flexible pad 29 to direct ultrasonic energy to the tooth or implant to be treated and to cushion the opposing teeth 31 while the bone healing device 38 is being held in place by the teeth 31 during the treatment.

Figure 9:
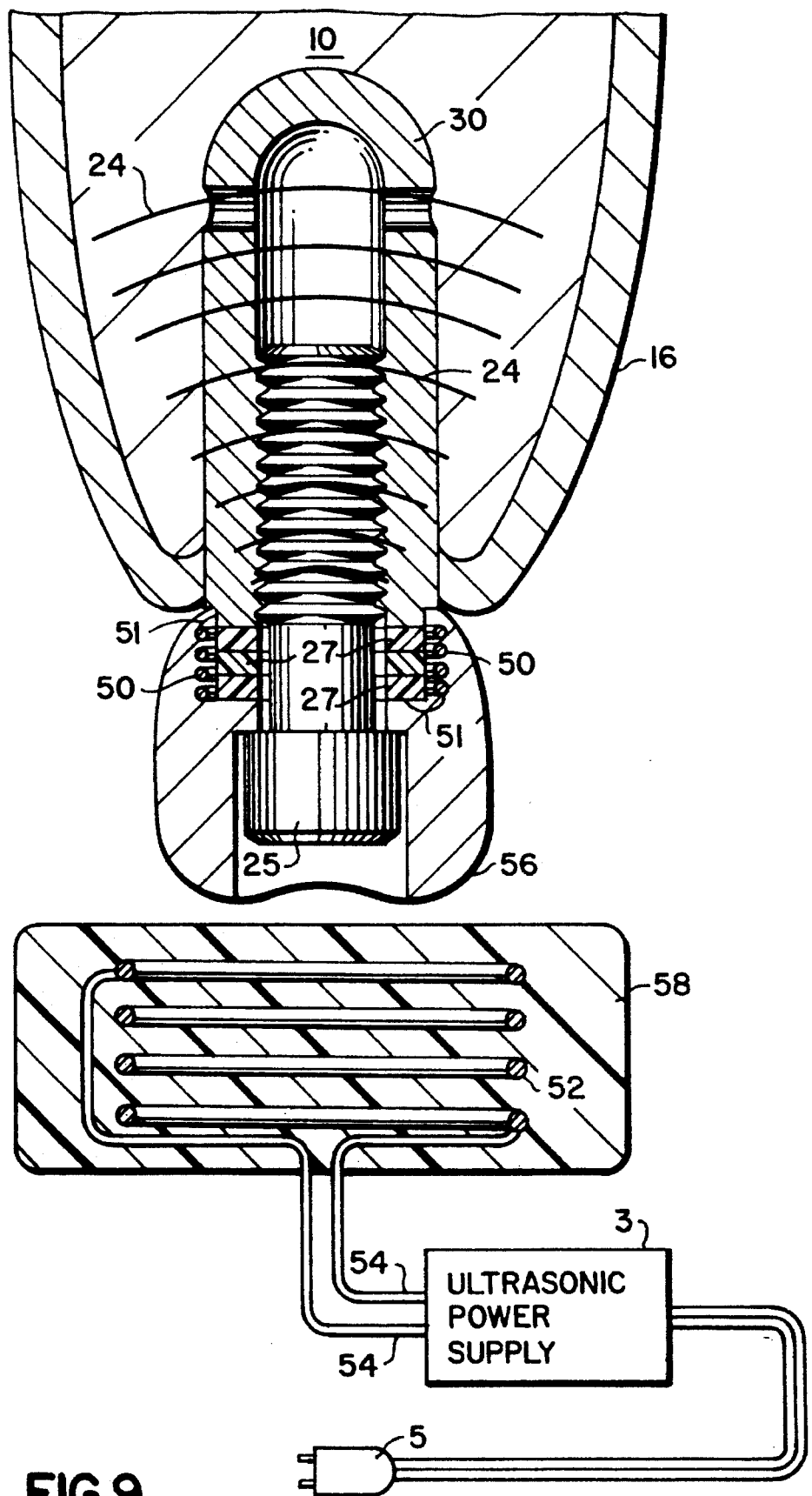
FIG. 9 shows an osseointegration application where the transducer produces ultrasonic energy for transmission to the jawbone through the implant.

FIG. 9 shows a multilayer piezoelectric transducer 27 having an induction coil 50 with wires 51 connecting the coil 50 to the transducer 27. The coil 50, transducer 27 and wires 51 are encapsulated within an artificial tooth 56 which may be directly attached to the implant 30 by a bolt 25 to thereby transmit ultrasonic wave 24 vibrations to the jawbone 10. The ultrasonic frequency electrical current may be generated by the ultrasonic power supply 3 is connected by wires 54 to an induction coil 52 which inductively couples the ultrasonic frequency electrical current to coil 50 encapsulated within the artificial tooth 56. The coil 52 may be encapsulated in an insulating material 58, as shown. The advantage of this embodiment is that the transducer 27 can be permanently or temporarily installed by the physician and the implant 30 is not disturbed during the osseointegration process. This embodiment provides a permanently sealed design and eliminates the electrical connections that the patients may find troublesome. The coil 52 can be placed outside the oral cavity on the outside of the face and held in place comfortably by the patient during the daily treatment. Alternatively, the coil 52 may be positioned proximate the implant 30 in the mouth.

While the preceding description contains many specificities, these should not be construed as limitations on the scope of the invention, but rather as an exemplification of a preferred and additional embodiments thereof. Many other variations are possible. Skilled artisans will readily be able to change dimensions, shapes and construction materials of the various components described in the embodiments and adopt the invention to all types of sonic energy applications, from subsonic through sonic to the ultrasonic range. Accordingly, the scope of the invention should be determined not by the embodiments illustrated, but by the appended claims and their legal equivalents.

What is claimed is:

1. An apparatus for accelerating the process of osseointegration of an implant in the jawbone in a patient comprising, a piezoelectric transducer constructed of at least one active element for contracting and expanding volumetrically when energized in response to a changing electrical field and generating vibrations of ultrasonic energy, said transducer transmitting said vibrations through the implant toward the jawbone when so energized, a threaded bolt for securing the piezoelectric transducer to the implant to transmit ultrasonic energy through the implant into the jawbone, and coupling means coupled to the piezoelectric transducer to transmit ultrasonic frequency electrical signals to said piezoelectric transducer.

2. Apparatus as defined in claim 1 wherein said implant includes an outer end, said transducer being held in direct contact with said outer end by said threaded bolt.

3. Apparatus as defined in claim 1 wherein said coupling means includes an induction coil connected to said transducer.

4. An apparatus operative in an area to be treated for accelerating the process of jawbone healing and regeneration or reattachment of a traumatically loosened tooth to the jawbone, comprising a piezoelectric transducer constructed of at least one active element for contracting and expanding volumetrically when energized in response to changing electrical signals and generating vibrations of ultrasonic energy, said transducer transmitting said vibrations to the jawbone through the soft tissue surrounding the jawbone when so energized, a cast formed of flexible material, said cast including a first portion disposed adjacent the crown of the tooth and a second portion which extends from said first portion, said second portion conforming to and engaging the soft tissue adjacent the area to be treated, said piezoelectric transducer being embedded within said second portion of the cast at a location remote from said first portion and from the crown of the tooth, and coupling means coupled to the piezoelectric transducer to transmit ultrasonic frequency electrical signals to said piezoelectric transducer.

5. Apparatus as defined in claim 4 wherein said cast includes an interior surface, a pocket formed in said interior surface and being spaced from said transducer, said cast having portions formed thereon which extend around said pocket adopted for engaging the soft tissue and sealing the pocket relative to the soft tissue, and further comprises a body of soft ultrasonic energy transmitting media disposed within said pocket.

6. An apparatus for accelerating the process of oseointegration of the jawbone of a patient with the outer bone engaging surface of an implant having an outer end for receiving a prosthesis, comprising a piezoelectric transducer constructed of at least one active element for contracting and expanding volumetrically when energized in response to changing electrical signals and generating vibrations of ultrasonic energy, said transducer transmitting said vibrations to the jawbone through the soft tissue surrounding the jawbone when so energized, a cast formed of flexible material, said cast including a first portion disposed adjacent the outer end of the implant and a second portion which extends from said first portion, said second portion conforming to and engaging the soft tissue, said piezoelectric transducer being embedded within said second portion of the cast at a location remote from said first portion and from the outer end of the implant, and coupling means coupled to the piezoelectric transducer to transmit ultrasonic frequency electrical signals to said piezoelectric transducer.

7. Apparatus as defined in claim 6 wherein said cast includes an interior surface, a pocket formed in said interior surface and being spaced from said transducer, said cast having portions formed thereon which extend around said pocket adopted for engaging the soft tissue and sealing the pocket relative to the soft tissue, and further comprises a body of soft ultrasonic energy transmitting media disposed within said pocket.

8. An apparatus operative in an area to be treated for accelerating the process of jawbone healing and regeneration or reattachment of traumatically loosened teeth to the jawbone, comprising a piezoelectric transducer constructed of at least one active element for contracting and expanding volumetrically when energized in response to changing electrical signals and generating vibrations of ultrasonic energy, said transducer transmitting said vibrations through a tooth toward the jawbone when so energized, a transducer support pad, an end cap comprising a one-piece solid molded body which is adapted to fit and engage the crown of at least one tooth, said transducer being sandwiched between and engaging said pad and said end cap, and coupling means coupled to the piezoelectric transducer to transmit ultrasonic frequency electrical signals to said piezoelectric transducer.

9. Apparatus as defined in claim 8 wherein said pad is flexible and is formed of a material which attenuates the emission of ultrasonic energy.

10. An apparatus for accelerating the process of oseointegration of the jawbone of a patient with the outer bone engaging surface of an implant having an outer end for receiving a prosthesis, comprising a piezoelectric transducer constructed of at least one active element for contracting and expanding volumetrically when energized in response to a changing electrical field and generating vibrations of ultrasonic energy, said transducer transmitting said vibrations through the implant toward the jawbone when so energized, a transducer support pad, an end cap having a recess therein providing a close fit to and energizing engaging the outer end of the implant, said transducer being sandwiched between and engaging said pad and said end cap, and coupling means coupled to the piezoelectric transducer to transmit ultrasonic frequency electrical signals to said piezoelectric transducer.

11. Apparatus as defined in claim 10 wherein said pad is flexible and is formed of a material which attenuates the emission of ultrasonic energy.

12. An apparatus for accelerating the process of oseointegration of an implant in the jawbone in a patient wherein the implant is covered with a soft tissue flap, comprising a piezoelectric transducer constructed of at least one active element for contracting and expanding volumetrically when energized in response to changing electrical signals and generating vibrations of ultrasonic energy, said transducer transmitting said vibrations through the soft tissue flap and the implant toward the jawbone when so energized, a transducer support pad, an end cap having a surface which is adapted to conform to the shape of and adapted to engage the soft tissue flap, said transducer being sandwiched between and engaging said pad and said end cap, and coupling means coupled to the piezoelectric transducer to transmit ultrasonic frequency electrical signals to said piezoelectric transducer.

13. Apparatus as defined in claim 12 wherein said pad is flexible and is formed of a material which attenuates the emission of ultrasonic energy.

* * * * *